United States Patent [19]
Majlessi

[11] Patent Number: 5,924,423
[45] Date of Patent: Jul. 20, 1999

[54] DEVICE FOR REDUCING SYMPTOMS OF PROLAPSED HEMORRHOIDS

[75] Inventor: Heshmat Majlessi, 233 Purchase St., Rye, N.Y. 10580

[73] Assignee: Heshmat Majlessi, Rye, N.Y.

[21] Appl. No.: 08/841,453

[22] Filed: Apr. 22, 1997

[51] Int. Cl.⁶ .................................................. A61M 29/00
[52] U.S. Cl. ........................... 128/897; 600/29; 606/197
[58] Field of Search .................................. 606/191–194, 606/196–197; 600/29–32; 128/897–98, DIG. 25

[56] References Cited

U.S. PATENT DOCUMENTS

| | | | |
|---|---|---|---|
| 4,938,221 | 7/1990 | Tuffel | 606/197 |
| 5,178,627 | 1/1993 | Hudock | 606/197 |
| 5,509,427 | 4/1996 | Simon et al. | 600/29 |
| 5,693,001 | 12/1997 | Salama | 600/29 |

*Primary Examiner*—John P. Lacyk

[57] ABSTRACT

The device for reducing the symptoms of prolapsed hemorrhoids has a continuous contour and a bulbous portion between leading and trailing ends of the device. The bulbous portion has a leading inclined surface and a trailing inclined surface which meet at an intermediate point of maximum radial dimensions. A rounded tip is provided at the leading end and a stop plate at the trailing end to control the extent of insertion.

20 Claims, 1 Drawing Sheet

DEVICE FOR REDUCING SYMPTOMS OF PROLAPSED HEMORRHOIDS

BACKGROUND OF THE INVENTION

1. Field of the Invention

The invention generally relates to medical devices and, more specifically to a device for reducing the symptoms of prolapsed hemorrhoids.

2. Description of the Prior Art

Forty million Americans suffer from hemorrhoids. Yet there is no effective device to relieve symptoms other than surgery. At this time prolapsed hemorrhoids are pushed back into the rectum manually, patients being instructed to use a glove to accomplish this task. Certain commercial preparations, such as "Anusol" and "Preparation H", improve the symptoms briefly but have no effect on congestion and actual treatment of the condition itself.

SUMMARY OF THE INVENTION

It is an object of the invention to provide a device for relieving the symptoms of hemorrhoids.

It is another object of the invention to provide a device as in the previous object which is effective and easy to use.

It is still another object of the invention to provide a device as suggested which is simple in construction and inexpensive to manufacture.

It is yet another object of the invention to provide a device as in the previous objects which can be marketed as a kit containing a number of differently dimensioned devices to be useful to many users.

In order to achieve the above objects and others which will become apparent hereinafter, a device for relieving the symptoms of prolapsed hemorrhoids comprises a generally cylindrical elongate body having leading and trailing ends and defining a longitudinal axis. The external surface of said body has a generally smooth contour formed as a surface of revolution said axis and forms a bulbous portion between said leading and trailing ends to create a gradually leading inclined surface and a gradually trailing inclined surface which meet at an intermediate point of said bulbous portion of maximum radial dimension. Said leading end has a rounded tip along said axis to facilitate insertion. Stop means is provided at said trailing end for controlling the extent of insertion, whereby the device can be optimally positioned to maintain said bulbous portion in contact with the hemorrhoids and reduce inflammation and swelling.

BRIEF DESCRIPTION OF THE DRAWING

The novel features of the invention, as well as the invention itself, both as to its structure and its operation, will be best understood from the accompanying drawings, taken in conjunction with the accompanying description, in which similar reference characters refer to the same or similar parts throughout.

The single FIGURE is a side elevational view of the device in accordance with the invention.

DESCRIPTION OF THE PREFERRED EMBODIMENT

Figure 1:
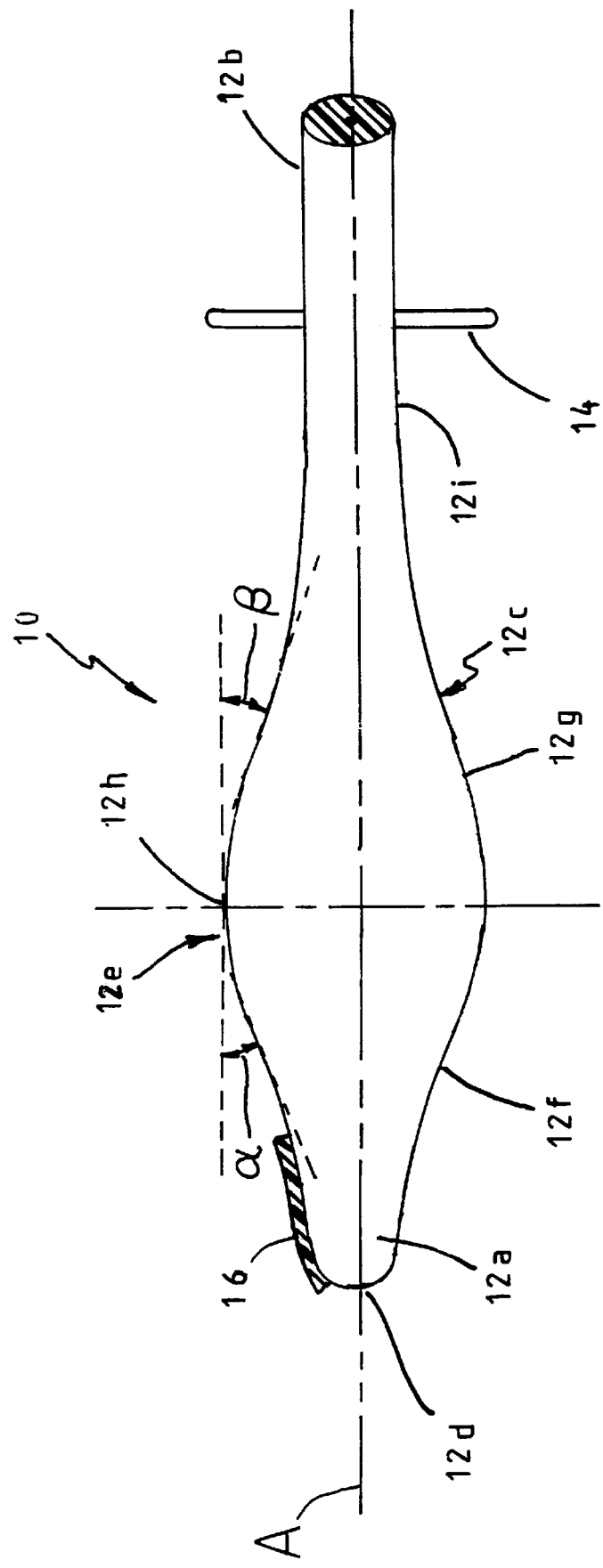

The device for reducing the symptoms of prolapsed hemorrhoids is designated by the reference numeral 10 in the single FIGURE.

The device 10 is formed of a generally cylindrical elongate body 12 having a leading end 12a and a trailing end 12b and defines a longitudinal axis A.

The external surface of the body 10 has a generally smooth contour formed as a surface of revolution of a curve 12c about the axis A. The leading end 12a is formed with a small rounded tip 12d along the axis to facilitate easy and painless insertion into the rectum with minimal damage to sensitive hemorrhoid tissues.

A bulbous portion 12e is formed between the leading and trailing ends 12a, 12b to create a gradually leading inclined surface 12f and a gradually trailing inclined surface 12g which meet at an intermediate point 12h of the bulbous portion 12e of maximum radial dimension. Although the specific maximum radial dimension at 12e is not critical it is presently preferred that this dimension be within the range of ⅓ in.–1 in. Also, the specific curvature of the leading inclined surface 12f and of the trailing inclined surface 12g is not critical. Thus, each of these surfaces may be conical or the like, as long as the transitions or points of inflection along the axis A are smooth and, preferably, gradual to facilitate use. In the illustrated embodiment the leading inclined surface 12f generally forms an angle a preferably less than 45° and the trailing inclined surface 12g generally forms an angle $\beta$ also preferably less than 45° in order to facilitate insertion and removal of the device after use. It is presently preferred that the angle $\alpha$ be within the range of 30°–75° and the angle $\beta$ be within the range of 10°–65°. It is clear from the FIGURE that the inclined surfaces 12f and 12g need not define uniform or continuous angles but may be tapered. Thus, the angle $\beta$ is essentially 0° at 12h and again reverts to 0° at 12i.

The small preferably spherical tip 12d allows painless insertion through the hemorrhoids. The gradual increase in diameter of the body 12 reduces prolapsed hemorrhoids. The large central part or bulbous portion 12e is dimensioned to apply continuous pressure on the hemorrhoids and thus reduce inflammation and swelling. The narrow shaft at the trailing end 12b keeps the patient comfortable while the device is in place.

In the presently preferred embodiment the angle $\beta$ is smaller than the angle $\alpha$, so that removing of the device 10 will apply less pressure on the hemorrhoid tissues as when the device is initially inserted and will be less likely to pull out the hemorrhoids when the device is removed. Naturally, as the angle $\alpha$ is increased the device will progressively increase the pressure on the hemorrhoids. Although this will tend to increasingly push the hemorrhoids in it may be more painful. Therefore, a series of such devices with increasing angles $\alpha$ may be effective over an extended period of treatment. Similarly, the angle $\beta$ may be gradually increased once the hemorrhoids start to shrink and are less likely to be pulled out be the device, resulting in shorter or smaller devices 10. By selecting the proper combinations of $\alpha$, $\beta$ and maximum diameter at 12h for the devices to be used initially and those to be used at the end of treatment, optimal benefits can be obtained with minimal trauma.

A plate 14 is provided at the trailing end which serves as a stop for controlling the extent of insertion. In this way the plate 14 may be located to optimally place or position the bulbous portion 12e at the most effective location which maintains continuous pressure on the hemorrhoids and reduce inflammation and swelling.

Preferably, disposable covers 16, of any suitable material such as paper or plastic, may be used to maintain the body 12 clean and sanitary and avoid the need for continuous cleaning.

The device 10 can be sold as part of a kit consisting of a plurality of such devices having different sizes and configurations together with a supply of disposable paper covers or the like. Thus, for example, in a kit of three devices the angle a can be progressively increased from 30° to 50° to 75°, while the angle β can be progressively increased from 10° to 25° to 60°. The maximum dimension at 12e can be maintained the same on the three devices in the kit or, preferably, this dimension is also increased to reflect the reduction in the swelling or contraction in the hemorrhoids.

In use the device 10 is covered with a cover 16 and the plate 14 is adjusted. The device is best used during a shower or a sitz bath. Instead of manual insertion this device simply and safely pushes the hemorrhoids back into the rectum without the unpleasantness of the existing procedures.

What has been described is a preferred embodiment of the invention, which is only given by way of example. Numerous modifications can be made to the disclosed embodiment without departing from the spirit of the invention. It is, therefore, the intention that the invention not be limited by the details of the preferred embodiment only by the scope of the claims which are appended hereto.

I claim:

1. Device for reducing the symptoms of prolapsed hemorrhoids comprising a generally cylindrical body having leading and trailing ends and defining a longitudinal axis, the external surface of said body having a generally smooth contour formed as a surface of revolution about said axis and forming a bulbous portion between said leading and trailing ends to create a gradually leading inclined surface that forms an angle α with a direction parallel to said axis, adapted to apply first axial pressures on the hemorrhoids during insertion of the device into the rectum and a gradually trailing inclined surface that forms an angle β with a direction parallel to said axis which is less than said angle α, adapted to apply second axial pressures less than said first axial pressures on the hemorrhoids during withdrawal of the device from the rectum, said leading and trailing ends meeting at an intermediate point of said bulbous portion of maximum radial dimensions adapted to provide desired radial pressure on the hemorrhoids, said leading end having a small rounded tip along said axis to facilitate easy and painless insertion into the rectum in the presence of hemorrhoids; and stop means at said trailing end for controlling the extent of insertion, whereby the device is optionally positioned to maintain said bulbous portion in contact with the hemorrhoids and reduce inflammation and swelling of hemorrhoids after being introduced into the rectum.

2. A device as defined in claim 1, wherein said leading inclined surface is generally conical.

3. A device as defined in claim 1, wherein said trailing inclined surface is generally conical.

4. A device as defined in claim 1, wherein said rounded tip is spherical.

5. A device as defined in claim 1, wherein α=β.

6. A device as defined in claim 1, wherein α>β.

7. A device as defined in claim 1, further comprising a cover for covering said body during use.

8. A device as defined in claim 7, wherein said cover is in the form of a disposable sleeve.

9. A device as defined in claim 8, wherein said cover is formed of paper.

10. A device as defined in claim 8, wherein said cover is formed of thin and compliant plastic sheet material.

11. A device as defined in claim 1, wherein α<45°.

12. A device as defined in claim 1, wherein β<45°.

13. A device as defined in claim 1, wherein 30°<α<75°.

14. A device as defined in claim 1, wherein 10°<β<65°.

15. A kit for reducing the symptoms of prolapsed hemorrhoids comprising a plurality of different devices each of which includes a generally cylindrical body having leading and trailing ends and defining a longitudinal axis, the external surface of said body having a generally smooth contour formed as a surface of revolution about said axis and forming a bulbous portion between said leading and trailing ends to create a gradually leading inclined surface that forms an angle α with a direction parallel to said axis, adapted to apply first axial pressures on the hemorrhoids during insertion of the device into the rectum, and a gradually trailing inclined surface that forms an angle β with a direction parallel to said axis which is less than said angle α, adapted to apply second axial pressures less than said first axial pressures on the hemorrhoids during withdrawal of the device from the rectum, said leading and trailing ends meeting at an intermediate point of said bulbous portion of maximum radial dimensions adapted to provide desired radial pressure on the hemorrhoids, said leading end having a small rounded tip along said axis to facilitate easy and painless insertion into the rectum in the presence of hemorrhoids; and stop means at said trailing end for controlling the extent of insertion, whereby the device is optimally positioned to maintain said bulbous portion in contact with the hemorrhoids and reduce inflammation and swelling of the hemorrhoids after being introduced into the rectum.

16. A device as defined in claim 15, wherein said devices in said kit have different sizes.

17. A device as defined in claim 15, wherein said devices in said kit have different configurations.

18. A device as defined in claim 15, wherein said devices in said kit have different leading and trailing surface inclinations.

19. A device as defined in claim 15, wherein the kit includes three devices.

20. A device as defined in claim 15, wherein α=30° and β=10° for said first device, α=50° and β=25° for said second device and α=75° and β=60° for said third device.

* * * * *